United States Patent [19]

Comeyne

[11] Patent Number: 4,948,973

[45] Date of Patent: Aug. 14, 1990

[54] NONLINEAR OPTICAL INTERROGATION SYSTEM

[75] Inventor: Robert G. Comeyne, Stafford, Va.

[73] Assignee: The United States of America as represented by the Secretary of the Army, Washington, D.C.

[21] Appl. No.: 797,284

[22] Filed: Oct. 2, 1985

[51] Int. Cl.⁵ .............................. G01J 1/00; G01J 3/30
[52] U.S. Cl. .................................... 250/341; 250/342; 356/318
[58] Field of Search ............... 250/330, 341, 342, 339; 356/318

[56] References Cited

U.S. PATENT DOCUMENTS

| | | | |
|---|---|---|---|
| 3,675,039 | 7/1972 | Boyd et al. | 250/330 |
| 4,112,300 | 9/1978 | Hall et al. | 250/330 |
| 4,422,758 | 12/1983 | Godfrey et al. | 250/341 |
| 4,496,839 | 1/1985 | Bernstein et al. | 250/341 |
| 4,500,784 | 2/1985 | Hacskaylo | 250/341 |

Primary Examiner—Stephen C. Buczinski
Attorney, Agent, or Firm—Milton W. Lee; John E. Holford; Anthony T. Lane

[57] ABSTRACT

A method and means for detecting the presence of infrared radiation and/or the presence of an optical dielectric transmitting element, such as a lens or window, is provided. By correlating the radiation wavelength with a visible detector wavelength and a specific dielectric element, the element can be identified or the alignment of a beam of radiation passing through the element can be established. In some cases the presence of a quiescent radiation device can be deduced from the identification of the dielectric element.

4 Claims, 2 Drawing Sheets

NONLINEAR OPTICAL INTERROGATION SYSTEM

The invention described herein may be manufactured, used, and licensed by the U.S. Government for governmental purposes without the payment of any royalties thereon.

BACKGROUND OF THE INVENTION

1. Field of the Invention

The invention relates to radiant energy detection systems particular those which employ far-infrared detectors and lasers.

2. Description of the Prior Art

There are a number of ways that far-infrared has been employed in military, medical, and civilian environments. In particular, passive detection systems are possible in total darkness when the targets generate heat signatures which can be distinguished from a cool background. Conversely a heated background can reveal a cool target. In daylight these systems present an added dimension to visible surveillance systems which is invaluable. The addition to such systems of an active source such as a laser adds still another dimension. The laser can be combined with the detector through circuitry which determines range, azimuth and other characteristics of targets detected. The fact that such systems emit no visible radiation presents, not only, a problem for their targets in warfare, but can also cause problems for the system users and designers as well.

SUMMARY OF THE INVENTION

In accordance with the present invention a peculiar phenomenon which occurs in certain elements of the above systems is employed to solve some of the problems these systems present. These elements, which may be lenses, prisms or windows, are often made of polycrystalline nonlinear optical materials, which not only refract and/or pass infrared or far-infrared radiation, but exhibit additional qualities which are useful to the present invention. When illuminated with infrared or far-infrared illumination from a Q-switched laser these elements generate characteristic harmonic radiations in the visible range which can be detected with the naked eye or an optical detector. Thus the IR illuminating beam may be used to detect the presence of a particular dielectric optical material or the reverse.

DESCRIPTION OF THE PREFERRED EMBODIMENTS

Figure 1:
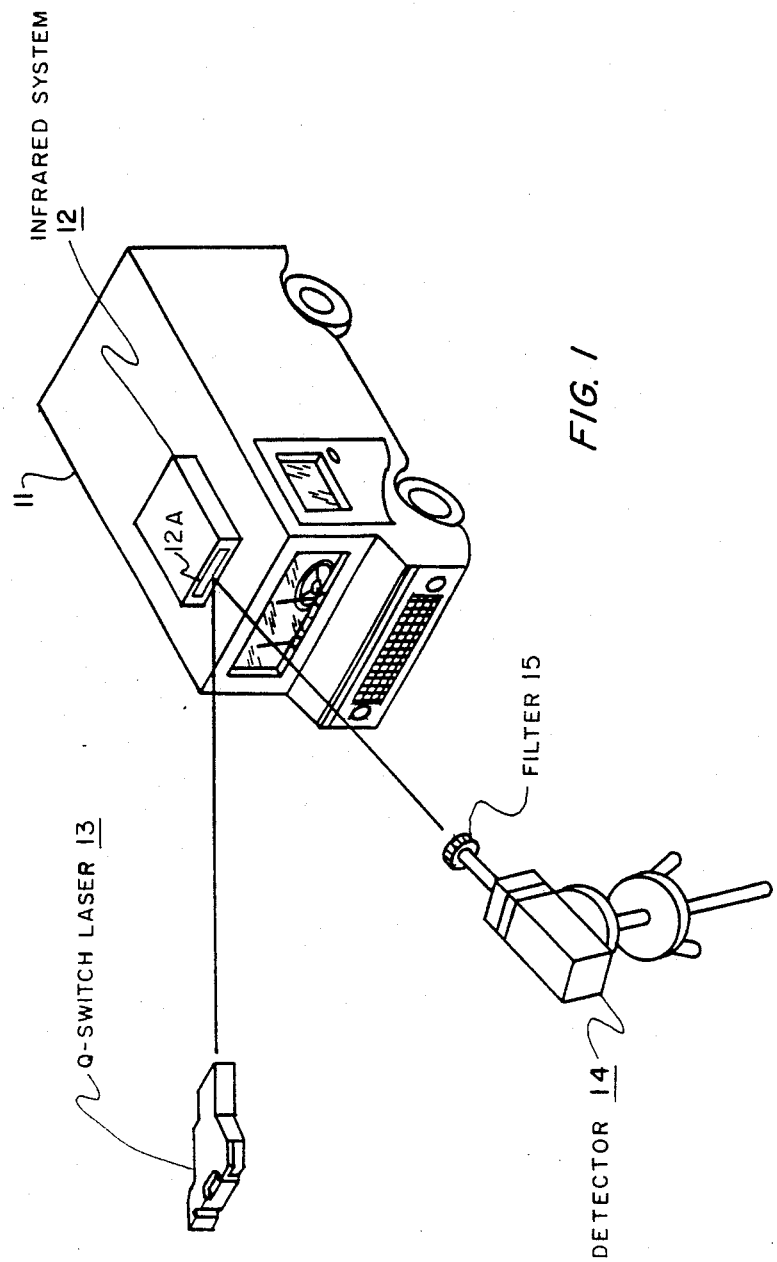
FIG. 1 shows a one embodiment of a detection system to determine the presence of an optical dielectric element.

Referring to FIG. 1 there is shown an embodiment including a target element of military equipment such as a vehicle 11 with an infrared system 12 such as a FLIR type far-infrared surveillance system, a laser rangefinder, or it could be simply a rifle sight or a pair of infrared binoculars. Any of these infrared systems can have lens or window 12A of the type previously mentioned. At a first remote site a Q-switch laser 13 is positioned with its beam directed onto the lens or window of the infrared system 12. At another remote site is positioned a detector 14 on which is mounted a filter 15 with a pass band in the visible spectrum. As the Q-switched laser beam from laser 13 passes through the lens, the nonlinear polycrystalline material of the lens or window produces harmonics of the laser radiation which are reradiated through the filter to the detector. If the infrared system 12 uses a Q-switched laser, it may also produce harmonic radiations that are picked up by the detector.

A more specific example of the above arrangement might be a target element infrared system comprising a Q-switched $CO_2$ laser range finder having a window of zinc selenide through which the beam of the $CO_2$ laser is beamed. The Q-switch laser 13 may include a $YAG:Nd^{+3}$ crystal as its lasing medium. The $CO_2$ laser is nominally centered at a wavelength of $10.6\mu$. The Q-switched laser is centered at about $1.06\mu$ wavelength. The nonlinear action of the window results in a reradiated harmonic wavelength of $0.532=$ in the given region of the visible spectrum. This is enhanced by passage through the filter for relatively noise free detection by the detector 14. When the detector is a human eye the filter is preferably employed in a set of goggles which reduce background illumination to dark adapt the eye. An electronic detector, however, can be made more sensitive and is not as subject to fatigue.

Figure 2:
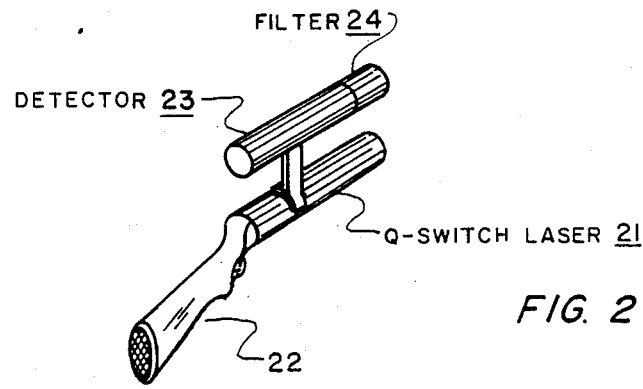
FIG. 2 shows a more integrated one man portable system of the type shown in FIG. 1.

FIG. 2 shows a modification of the FIG. 1 system. The Q-switched laser 21 is preferably mounted in a gunstock 22 or other portable handling structure, which is then easily adapted for a tripods or other fixed mounting as required. The detector 23 and/or visible light filter 24 with suitable optics, such a telescopic sight, is mounted on and above the laser and bore sighted therewith. The user may remove the filter to select a target then replace it and activate the laser to detect the presence of windows or lasers of the type described above. Additionally, an infrared nightsight (not shown) can be added which may be used either in daylight or at night in conjunction with the Q-switch laser. Once a target is acquired the visible sight and filter can be used to locate the window element, if present.

Figure 3:
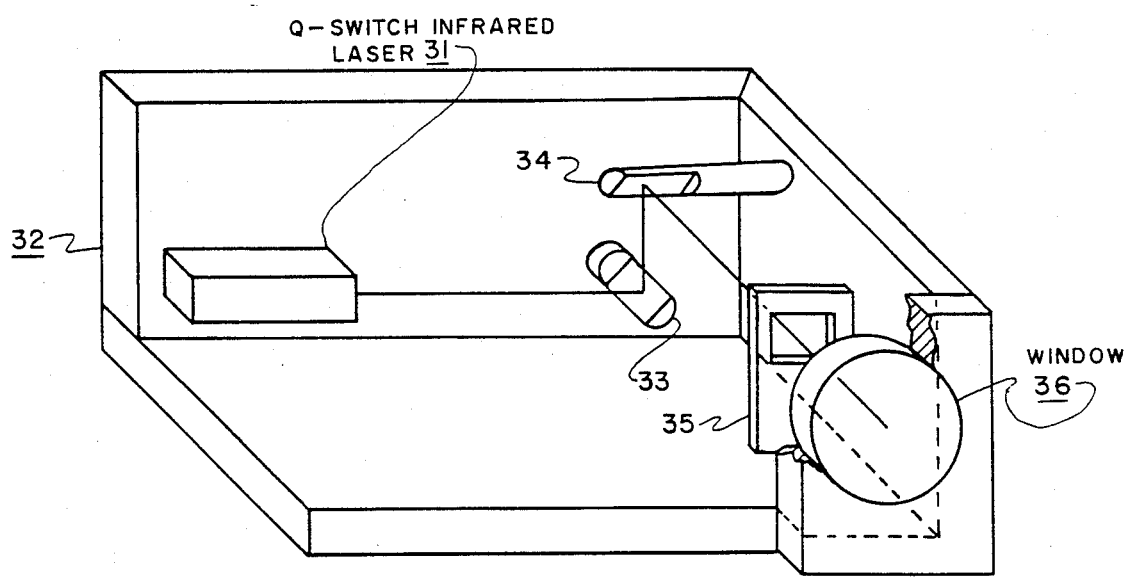
FIG. 3 shows an optical dielectric element used to align the beam of a laser.

FIG. 3 shows a correlative system which is quite common. A Q-switch infrared laser 31 is mounted on a base 32 with a metal deflection mirror 33 and an aperture. The mirror or mirrors 33 and 34 (if there is both horizontal and vertical deflection) rotates through a small angle to scan the beam over a major portion of the aperture in stop 35. Without a detector it is very difficult to tell when the scan is centered in the aperture or when the scan limits are properly set to keep the scan within the aperture. This can be simplified by using a polycrystalline window 36 or lens of a suitable material as indicated above. The window interacts with the beam to produce a visible image of the aperture when the beam angle is too wide. The beam can then be narrowed and recentered until a slight separation of the beam from all the edges of the aperture is noted.

As can be seen from the FIG. 1 system the reradiation effect in no way resembles the corner reflection type of effect that has been used to locate optical devices in the past. The radiation not only changes wavelength but is omnidirectional in character. While the FIG. 3 system is used with a scanning beam there are numerous laser applications wherein fixed beams are aligned with apertures, reflectors, and detectors; such as in navigation, communication, or land surveying systems that could employ this invention. While the target element has been described as a lens or window, it may be simply a marker or any other type element.

I claim:

1. In a system for detecting the presence of polycrystalline nonlinear optical materials typically used as optical transmission elements in an infrared detection system in a military environment, the system for detecting comprising:

means for irradiating said infrared detection system with a Q-switched laser beam in which said laser beam wavelengths are longer than visible spectrum wavelengths and in which nonlinear action of said optical transmission elements when irradiated with said Q-switched laser beam generates characteristic harmonic radiation in the visible spectrum; means for detecting said characteristic harmonic radiation reradiated from said infrared detection system; and means for identifying said polycrystalline nonlinear optical materials by including a bandpass filter means on the detecting means to pass only photons in a narrow band of visible wavelengths which identify the generated characteristic harmonic radiation of said optical materials normally used in said infrared detection systems and of the infrared radiation source of said detection systems.

2. A method for identifying the presence of passive polycrystalline nonlinear optical material target elements and active radiant energy in an infrared detection system which emits in the infrared spectrum, the steps comprising:

irradiating said infrared detection system with a laser beam from a Q-switched laser positioned in a remote site from said infrared detection system, in which said Q-switched laser beam wavelengths are no longer than wavelengths within the visible spectrum and in which the nonlinear action of said optical material target elements when irradiated with said Q-switched laser beam generates characteristic harmonic radiation in the visible spectrum; and detecting said characteristic harmonic radiation in the visible spectrum with a detector also positioned at a remote side wherein said detector has a filter means with a bandpass in the visible spectrum mounted thereon wherein said optical material target elements and the radiant energy source in said infrared detection system are identified by the detected characteristic harmonic radiation.

3. A method as set forth in claim 2 wherein said steps are specifically comprised of:

said step of irradiating is by a Q-switched laser using a YAF:$Nd^{+3}$ crystal as its lasing medium which is centered at about 1.06$\mu$m wavelength in which said infrared detection system being irradiated is comprised of a Q-switched $CO_2$ laser range finder centered at a wavelength of 10.6$\mu$m and having a window of zinc selenide through which the beam of said $CO_2$ laser is beamed wherein said nonlinear action of said zinc selenide when irradiated with said YAG:$Nd^{+3}$ crystal lasing medium laser beam generates a reradiated harmonic wavelength in the 0.532$\mu$m region of the visible spectrum; and said step of detecting said reradiated harmonic wavelength radiation is by passing said wavelength through a filter means selected to have a bandpass in the 0.532$\mu$m region in which detectable radiation represents the presence of zinc selenide typically used in an enemy military infrared detection system.

4. A method as set forth in claim 2 wherein said steps of irradiating and detecting remote sites are at the same site wherein said Q-switched laser is mounted on a portable handling structure and said filter and detector are foresighted with said Q-switched laser and wherein said step of detecting further comprises selectively using said filters according to the radiation wavelengths being identified.

* * * * *